United States Patent
Yershov et al.

(10) Patent No.: US 7,985,716 B2
(45) Date of Patent: Jul. 26, 2011

(54) NUCLEIC ACID SAMPLE PURIFICATION AND ENRICHMENT WITH A THERMO-AFFINITY MICROFLUIDIC SUB-CIRCUIT

(75) Inventors: Gennadiy M. Yershov, Willowbrook, IL (US); Alexander Kukhtin, Lockport, IL (US); Boris K. Chernov, Burr Ridge, IL (US); Julia B. Golova, Willowbrook, IL (US); Darrell P. Chandler, Manchester, MI (US)

(73) Assignee: UChicago Argonne, LLC, Chicago, IL (US)

( * ) Notice: Subject to any disclaimer, the term of this patent is extended or adjusted under 35 U.S.C. 154(b) by 615 days.

(21) Appl. No.: 11/744,112

(22) Filed: May 3, 2007

(65) Prior Publication Data

US 2008/0076677 A1 Mar. 27, 2008

Related U.S. Application Data

(60) Provisional application No. 60/826,812, filed on Sep. 25, 2006, provisional application No. 60/826,693, filed on Sep. 22, 2006.

(51) Int. Cl.
*C40B 60/10* (2006.01)
(52) U.S. Cl. .................................. 506/38; 506/3; 435/6
(58) Field of Classification Search .................... None
See application file for complete search history.

(56) References Cited

U.S. PATENT DOCUMENTS

| 2003/0190608 A1* | 10/2003 | Blackburn ........................ 435/6 |
| 2010/0216657 A1* | 8/2010 | Hukari et al. ..................... 506/9 |

* cited by examiner

*Primary Examiner* — Christopher M Gross
(74) *Attorney, Agent, or Firm* — Barnes & Thornburg LLP; Alice O. Martin

(57) ABSTRACT

Multiplexed affinity purification and thermal dissociation prior to biochip hybridization simplifies uncharacterized sample admixtures, thereby minimizing or eliminating sample interferents, improving hybridization specificity on a microarray detector, and minimizing or eliminating the need for post-hybridization thermal dissociation analysis. An integrated thermo-affinity sample preparation sub-circuit for sample purification and enrichment is described that is consistent with a field-portable form factor and analytical processes. Thermo-affinity sample preparation on model admixtures of varying complexity was efficacious.

15 Claims, 7 Drawing Sheets

A.

B.

A.

B.

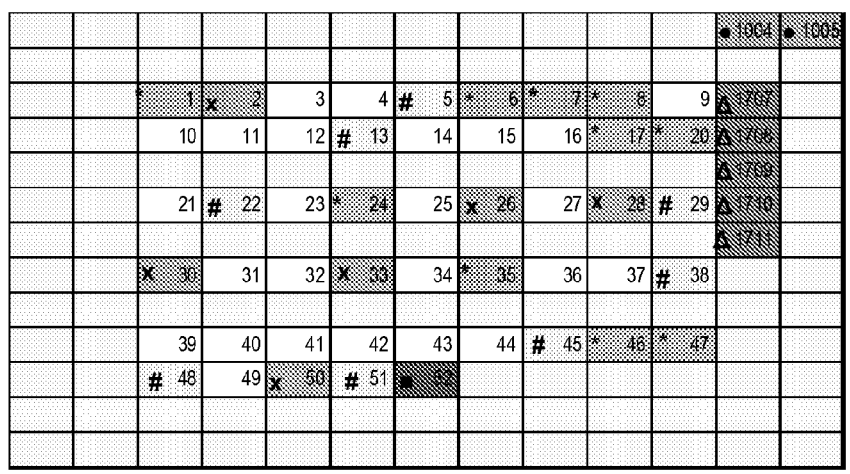

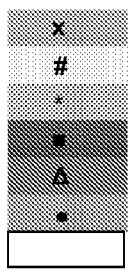 Indicates that the probe has complementary target in the model sample \# Indicates that the probe has complementary target in the model sample with T-tail ∗ Indicates that the probe does not have complementary or mismatch in the model sample ■ Indicates hybridization marker ▲ Indicates that the probe has complementary target in the model sample, which is specific to real organism.

● Indicates labeled probes that are show immobilization efficiency and provide mechanical biochip alignment for reading ☐ Indicates that the biochip element contains immobilized probe that may have mismatches in the model sample

FIG. 8

SEQUENCE LISTING

<160> NUMBER OF SEQ ID NOS: 82

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (13)..(13)
<223> OTHER INFORMATION: inosine

<400> SEQUENCE: 1
ctttrgaaaa tangagataa tt                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ttgagtaaat aggrtataat tg                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 3
ttgagtarat aagatataac tg                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
ttacccgatt ccrggttaat t                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 5
ttacccgatt ctrggttaat t                                               21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 6
gaggrtayac gaattactac                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 7
gtatttccgc attgtgaygc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 8 gtatttcgc attgagaygc                                                  20

```
<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tatacgttcg tgtgcagt                                                   18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gtaaatctgt tctatgctgt                                                 20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cttaaraaaa cgagtgataa tt                                              22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
yctgttacag tgtttaatag ttt                                             23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
aaacttgyca aagctgtyag a                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ttgataattr cattacggct a                                               21
```

-continued

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ttgataatca cattrcggct a                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)..(5)
<223> OTHER INFORMATION: inosine

<400> SEQUENCE: 16
taatnaygag acttctccag t                                              21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ttttacgatt gcctttytgg ata                                            23

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gttataatga ttgtagtatc c                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ttgaattgaa tarttcgtag t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aaatgctaag catgaatatg g                                              21

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
agatgctaag caygagtatg g                                              21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (5)..(5)
<223> OTHER INFORMATION: inosine

<400> SEQUENCE: 22
agtcntgata atayttggay gta                                            23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (17)..(17)
<223> OTHER INFORMATION: inosine

<400> SEQUENCE: 23
tttctaatac atsggtnaat ttgag                                          25

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
ataggcaatg ggrctgata                                                 19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (2)..(2)
<223> OTHER INFORMATION: inosine

<400> SEQUENCE: 25
gnttatttgc agttaarggg                                                20
```

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gtttattcgc agttaarggg                                                   20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cactgttgta gcaaatagg                                                    19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tcgtttagag gtgacgtcyt                                                   20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
rcataaatat aaacatagtg tg                                                22

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
acctaaaatc acgcaaagga tatcaa                                            26

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
atygatattr catcrttaac aag                                               23
```

```
<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aaaaycatct gaytaattat tctata                                              26

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tcacaataat ttaaaatgct ct                                                  22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
gtcgtcaata gcattaataa tac                                                 23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gtagccaata gcgttaataa ta                                                  22

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
gatgctaatg atatatttcc ata                                                 23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
acrttctatt gtgaaggtgc ytc                                                 23
```

```
<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
atatttcaag cyccatagta g                                              21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gagtgcccta atccagtg                                                  18

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
ctgtgttctt aggtattatg                                                20

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
attgcttacg gaggtgattt tg                                             22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
atcatttcca tgtagagttg c                                              21

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
tcttytgcac cctartcyat ttga                                           24
```

```
<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
gtycaattct accttctatg a                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gacttgraga ggtacrtttt c                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gacttggaga agtacatttt c                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
gcattrcttc tctgaatgaa t                                              21

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
agttagttgt aatccactat ac                                             22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
attttgcgat caatatacac at                                             22
```

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
gatgatgatg atgatgatga                                                  20

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tcaagagttg cccatcctgc agcaa                                            25

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
aacatcgctc ttgccacaga ctgcgtcagt                                       30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
ccagtgagtg acgactgatt tgcattccgg                                       30

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
tgcgatcagg aaatcaacca ga                                               22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
tctggttgat ttcctgatcg ca                                               22
```

```
<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
caattatayc ctatttactc aa                                              22

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
tatcagyccc attgcctat                                                  19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
cccyttaact gcgaataaac                                                 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
argacgtcac ctctaaacga                                                 20

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
cttgttaayg atgyaatatc rat                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
gtatagtgga ttacaactaa ct                                              22
```

```
<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
tttttaatta accyagaatc gggtaattttt t                                    31

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
tttttttttt tcaaatrgay tagggtgcar aagattttttt tttt                      44

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
tttttttttt ttttttctra cagctttgrc aagttttttt tttttttttt t               51

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
tttttttttt tttttttttt cctatttgct acaacagtgt tttttttttt ttttttttt       59

<210> SEQ ID NO 66
<211> LENGTH: 58
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
tttttttttt tttttttttt atgtgtatat tgatcgcaaa attttttttt tttttttt        58

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
tttttttttt tttttccata ttcatgctta gcattttttt tttttttttt t               51
```

```
<210> SEQ ID NO 68
<211> LENGTH: 43
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
tttttttttt tatggaaata tatcattagc atctttttt ttt                          43

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
tttttgaaaa tgtacttctc caagtctttt t                                      31

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
tcatcatcat catcatcatc                                                   20

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71 caattttttca gggaataaca ttg                                              23

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaagttcaga tcttgatgac attg                                              24

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcttatctgg atttaatgtc gc                                                22
```

```
<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcagctgtca cagtaacaaa cc                                              22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttataccact ctgcaacgtg tc                                              22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aactccatta acgccagata                                                 20

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 caattttca gggaataaca ttgctgcagg atgggcaact cttgagct                   48

<210> SEQ ID NO 78
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tttcaagtct agaactactg taacataaaa gagaattaat ttaaatataa atgtct          56

<210> SEQ ID NO 79
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcttatctgg atttaatgtc gcatagtgga acctcactga cgcagt                    46
```

```
<210> SEQ ID NO 80
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agtcgacagt gtcattgttt ggcattgtag cgagaacggt gtc                      43

<210> SEQ ID NO 81
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ttataccact ctgcaacgtg tcgcagcgct ggaacgttcc ggaatgc                  47

<210> SEQ ID NO 82
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttgaggtaat tgcggtctat actactttgg tcactcactg ctgactaaa                49
```

NUCLEIC ACID SAMPLE PURIFICATION AND ENRICHMENT WITH A THERMO-AFFINITY MICROFLUIDIC SUB-CIRCUIT

This application claims priority from copending U.S. Ser. No. 60/826,812 filed Sep. 25, 2006 and from U.S. Ser. No. 60/826,693 filed Sep. 22, 2006.

The United States Government has rights in this invention pursuant to Contract No. W-31-109-ENG-38 between the United States Government and The University of Chicago and/or pursuant to Contract NO. DE-AC02-06CH11357 between the United States Government and UChicago Argonne, LLC representing Argonne National Laboratory.

BACKGROUND

With the accelerated development and use of nucleic acid microarray technology, there is considerable interest in applying existing (off-the-shelf) microarray methods and devices in uncharacterized sample backgrounds, and developing microfluidic devices for near-instantaneous biodetection applications. Uncharacterized sample backgrounds create both a sample preparation and data interpolation challenge for diagnostic use of microarray technology, and a significant engineering challenge for packaging microarray processes within a sample-to-answer fluidic test cartridge. The challenges become even more acute within the context of environmental monitoring due to the co-extraction of soluble environmental constituents that interfere with molecular techniques (including PCR amplification, hybridization, and fluorescent detection) and the preponderance of unknown and uncharacterized non-target organisms in the biological background.

Theoretical and experimental data with planar and gel element arrays show that mismatched targets preferentially bind under non-equilibrium hybridization conditions, exacerbating the problem of false positive detection. Depending upon the nucleic acid purification and labeling strategy, non-target sequences can also contribute to increased local and global background, degrading overall system (sample-to-answer) performance and dynamic range. One strategy to address cross-hybridization in defined (or closed) biological systems is to remove unpredictable probes from the array. Another is to increase the total number of probes on an array and statistically compare the signal intensity between perfectly matched (PM) and single base mismatched (MM) duplexes, typifying re-sequencing array designs. Hybridization kinetics can also be used to de-convolve false-positives in defined biological systems, and temperature, ionic strength and chemical additives are well-known methods of influencing hybridization stringency. However, a question concerning the application of microarray technology in uncharacterized samples or open biological systems is: how is it possible to know if and when hybridization signals result from a perfectly matched or mismatched probe: target combination? In an uncharacterized sample, any detectable microarray signal (over background) may have practical importance (e.g. pathogen surveillance), and recent work indicates how PM and MM probe comparisons can be problematic (e.g. erroneous) in complex samples.

One approach to de-convolve false positive hybridizations on microarray substrates has been to generate post-hybridization thermal dissociation curves for every probe on the array. Historically, dissociation studies were aimed at understanding nucleotide mismatch discrimination, duplex stability and hybridization behavior in order to define an a priori hybridization conditions for generating unambiguous reads from the initial hybridization data Another way to utilize on-chip thermal dissociation, however, is as a post-hybridization, diagnostic indicator of hybridization specificity, utilizing curve shape and/or dissociation constants as part of the decision logic for data interpretation, being careful to account for thermal effects on commonly used fluorescent reporters.

From a sensor or biodetection technology perspective, post-hybridization thermal dissociation analysis is an exciting possibility for target-independent, diagnostic validation of hybridization specificity irrespective of a priori knowledge of target background. By itself, however, the technique does little to address the (fluidic or automated) nucleic acid sample preparation challenge or simplify the attendant analysis instrumentation.

SUMMARY

Multiplexed affinity purification and thermal dissociation prior to biochip hybridization simplifies uncharacterized sample admixtures, thereby minimizing or eliminating sample interferents, improving hybridization specificity on a microarray detector, and minimizing or eliminating the need for post-hybridization thermal dissociation analysis. An integrated thermo-affinity sample preparation sub-circuit for sample purification and enrichment is described that is consistent with a field-portable form factor and analytical processes. Thermo-affinity sample preparation on model admixtures of varying complexity was efficacious.

Thermo-affinity, multiplexed sample purification and enrichment in a microfluidic sub-circuit has been demonstrated and shown to be efficacious on oligonucleotide and gene fragment targets present at fmol quantities and at 1:10,000 in a non target background. Microarray profiles show reduced incidence of false-positive hybridization and retention of specific target signals after thermo-affinity sample purification.

BRIEF DESCRIPTION OF DRAWINGS

FIG. 8 is a map of the microarray with complementary probe numbers indicated.

DETAILED DESCRIPTION

Figure 2:
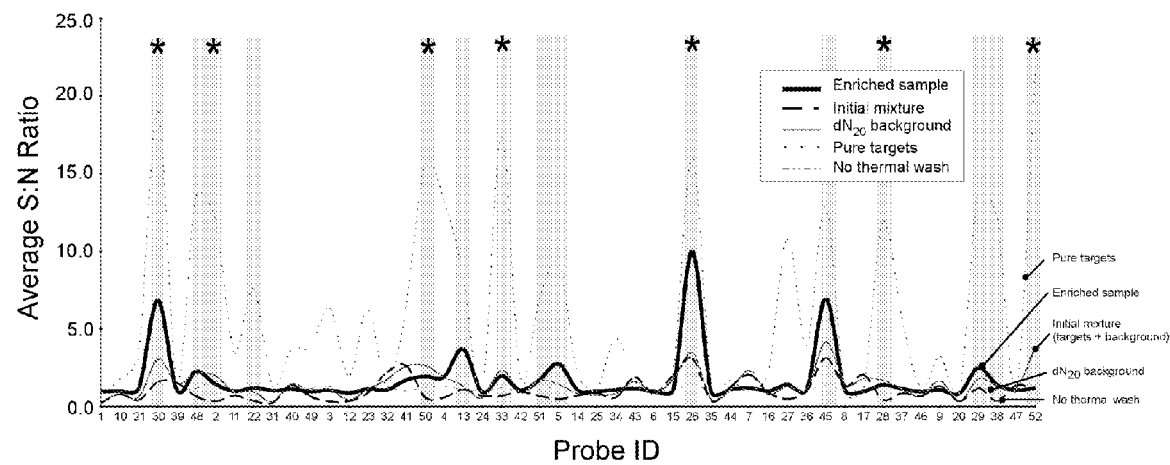
FIG. 2 shows graphical results of multi-template thermo-affinity enrichment in a microfluidic sub-circuit. Results are the average ratio (n=3 independent trials) of background-corrected probe intensity to background-corrected empty gel elements. Probe IDs are ordered according to their position on the array but correspond to Table 1 designations. Shaded grey boxes behind the curves identify probes with a perfect match to one of the synthetic targets in the sample mixture (PM and PM-T probe:target combinations in Table 1); asterisks indicate PM probe:target combinations only. Pure targets+hybridization marker (dotted grey line), the initial target mixture (heavy dashed line) and the dN20 background (solid grey line) were not pre-processed through the multiplexed affinity purification sub-circuit prior to hybridization.

Summary data for multiplexed, thermo-affinity sample preparation are shown in FIG. 2, where 12.5 fmol gl$^{-1}$ of each of 15 synthetic targets were diluted 1:10,000 into a background of 125 μmol μl$^{-1}$ dN$_{20}$ and processed as described herein (total sample input –15 μL). The pure target mixture by itself (at 1.25 fmol μl$^{-1}$ each target) showed significant levels of cross-hybridization (S:N ratios>1.2) to 26 non-target probes containing 1 or more mismatches to the oligonucleotide targets (50% of the array). Upon dilution into the dN$_{20}$ background and in the absence of thermo-affinity purification, 28 total probes resulted in S:N ratios>1.2, with 15 of these signals (30% of the array) representing mismatched probe:target combinations. The dN$_{20}$ background itself reacted with the immobilized probes, resulting in a S:N ratio>1.2 on 17 of 49 (35%) microarray probes. After thermo-affinity purification and enrichment, however, only 6 non-target probes generated signal significantly over background and of the six non-target probes, three were at the 1.2 S:N ratio threshold (probes 7, 21 and 43). However, FIG. 2 and Table 2 shows that all of the perfectly matched probe S:N ratios for the enriched sample were >1.2 and (except for probe 22) demonstrably greater than the non-target signals. Flow-through solutions from the sample preparation sub-circuit did not generate any detectable signal on the microarray. In the absence of a thermal wash in the sample preparation sub-circuit, S:N ratios for PM and PM-T probes were actually lower than the S:N ratios in the initial target mixture (inclusive of the dN2o background; FIG. 2). These data indicate that the sample preparation sub-circuit is effectively capturing, concentrating, and purifying target molecules from cross-reactive background and enhancing microarray discriminatory ability.

Data in Table 2 further show that multiplexed, thermo-affinity sample purification and enrichment was more efficacious for targets containing poly-T overhangs than for the shorter, perfect complements, in that average S:N ratios after sample preparation increased for all but one of the probe:target combinations (probe 38) relative to the average S:N ratio in the initial target+background mixture. This result was unanticipated, as the affinity purification sub-circuit does not contain any probes that would be expected to interact with the dangling ends of the targets. This result may be partially explained by non-canonical T-T base pairing between the single-stranded target molecules, resulting in target networking in the affinity purification sub-circuit 15. Regardless, the data demonstrate that multiplexed, thermo-affinity sample preparation can enrich a sample for target sequences and enhance detection sensitivity at the microarray (as indicated by improved average S:N ratios), given a target molecule present in a 10.000-fold excess of non-target background.

Figure 3:
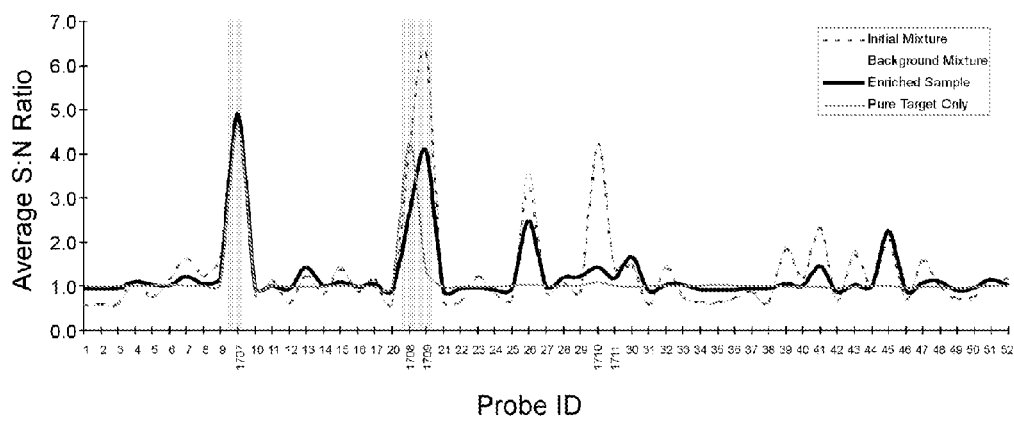
FIG. 3 shows graphical results of multi-template thermo-affinity enrichment of synthetic gene targets in a model PCR product cocktail. Results are the average ratio (n=4 independent trials) of background-corrected probe intensity to background-corrected empty gel elements. Shaded grey boxes behind the curves identify probes with a perfect match to one of the synthetic gene targets in the sample mixture. Probe IDs are as listed in Table 1.
Figure 4:
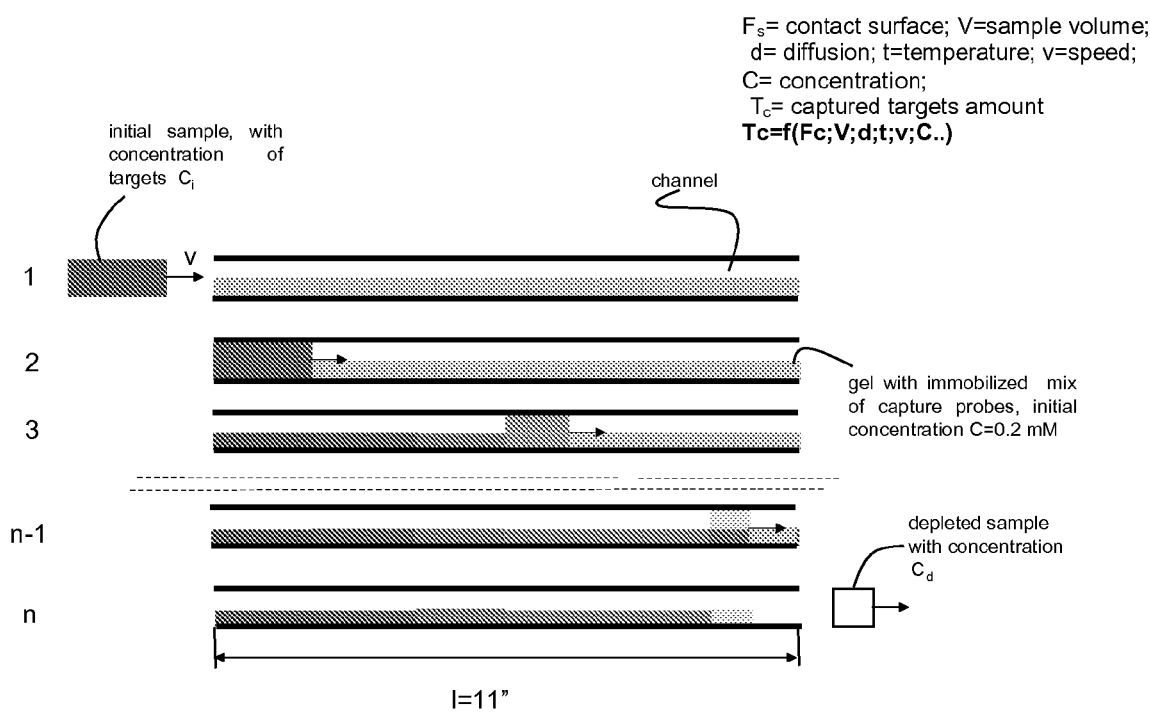
FIG. 4 illustrates the serpentine channel circuitry.
Figure 5:
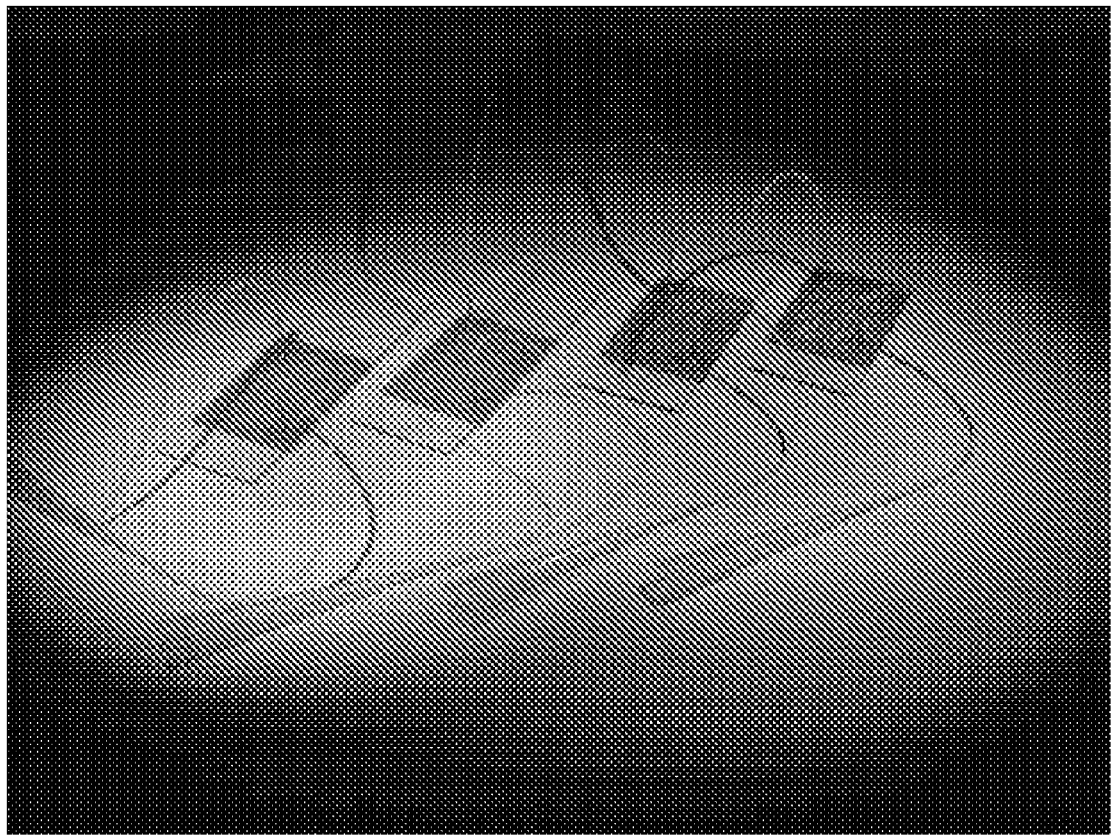
FIG. 5 shows multiple purification circuitry.
Figure 6:
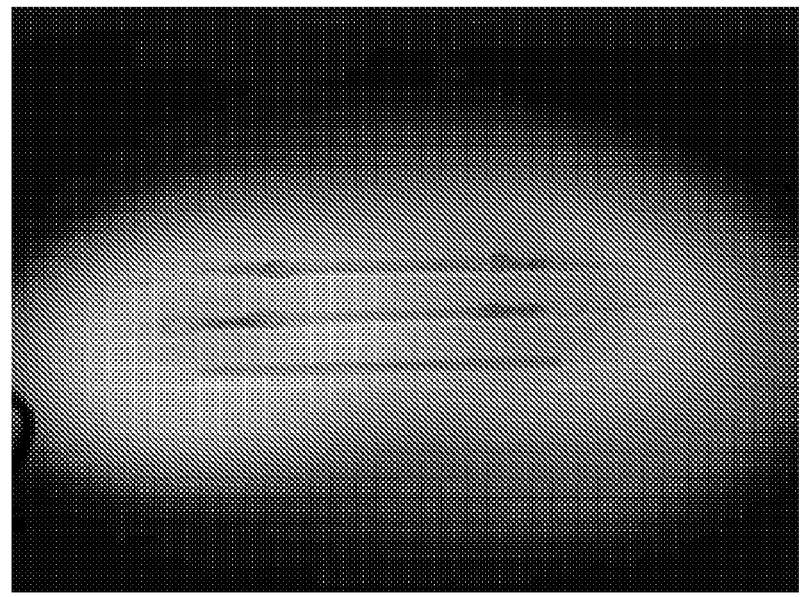
FIG. 6 shows a gel picture (A) and a dual gel circuitry (B).
Figure 6:
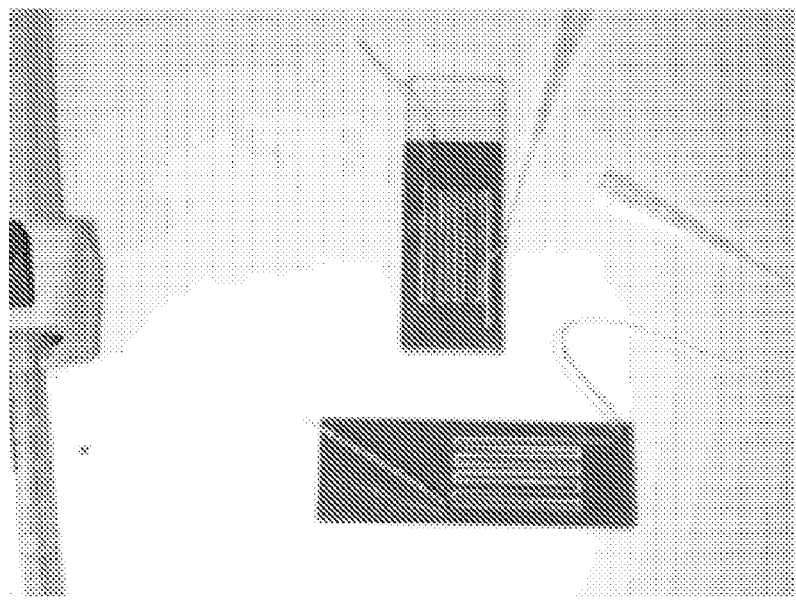
Figure 7:
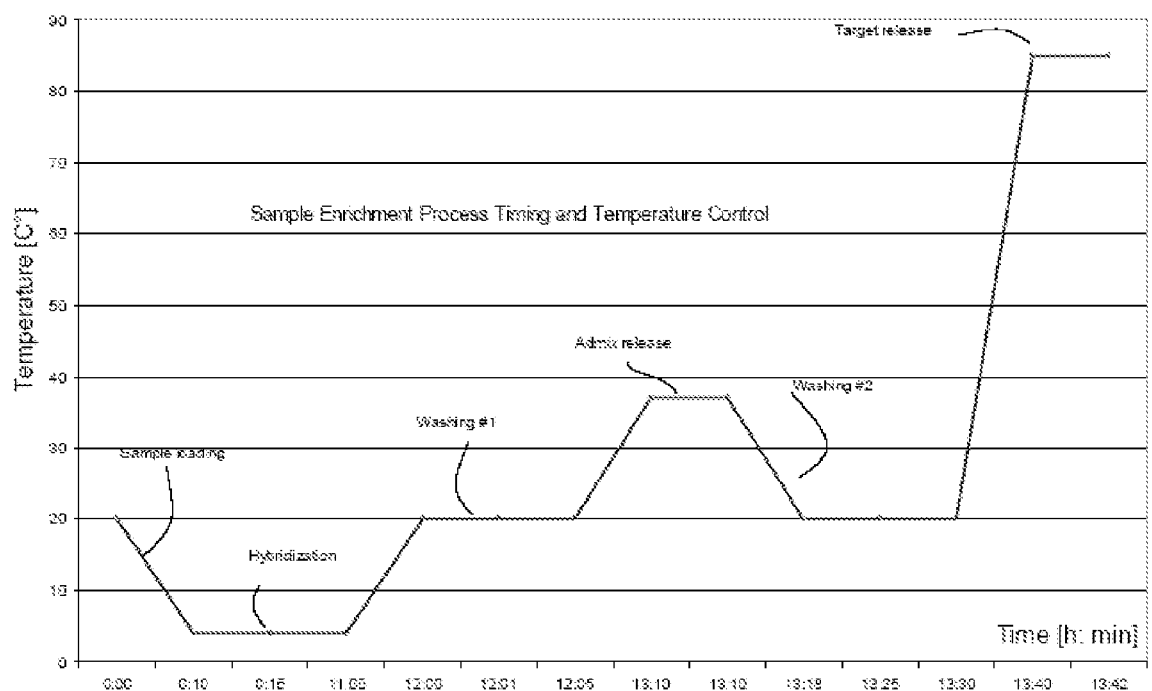
FIG. 7 shows sample enrichment process over time.

The proof-of-principle system was extended to a model polymerase chain reaction (PCR) product cocktail containing 125 μmol μL$^{-1}$ dN$_2$o background, 1 pmol 4-1 each of six PCR primers, and 12.5 fmol μL$^{-1}$ Texas Red-labeled, synthetic gene fragments (Table 1). In this system, the pure target mixture was very specific to its complementary probes under the conditions used here (FIG. 3). As with the synthetic oligonucleotide mixture, however, the dN$_{20}$ background cross-reacted to 24 probes at an average S:N ratio >1.2 (45% of the array) and dominated the profile of the initial target mixture (correlation=0.997). The non-target background+primer mix did not affect the microarray performance to the same extent that the non-target background interfered with synthetic oligonucleotide target hybridization, as indicated by the observed decrease in average S:N ratio for PM probes (FIG. 3 versus FIG. 2, grey highlights). After thermo-affinity sample preparation, however, the number of nontarget probes with an average S:N ratio >1.2 was reduced to 11 probes, with the overall array profile more closely resembling the pure target data (correlation=0.734) than the initial target mixture (correlation=0.609). Unlike the model system in FIG. 2, analysis of sample preparation flow-through resulted in detectable microarray signals on the *E. coli* 0157:H7 gene-specific probes, indicating that the sample preparation efficiency for the gene targets was lower than for the short oligonucleotide targets. The data show that thermo-affinity sample preparation can also enrich for target sequences typifying the products of a PCR or multiplex PCR assay, and reduce the incidence of non-specific hybridization at the microarray detector.

Hybridization specificity can be tuned by increasing hybridization temperature, modifying buffer compositions, or altering hybridization times and wash procedures to take advantage of kinetic effects 8. Thus, some of the non-specific microarray hybridization results in FIGS. 2 and 3 could be addressed at the point of microarray hybridization. Thermoaffinity sample preparation was evaluated as a mechanism to simplify and improve microarray hybridization specificity using a relatively low stringency, equilibrium hybridization condition in order to evaluate the efficacy of sample preparation sub-circuit. Because the thermo-affinity sub-circuit is likewise based on hybridization, all of the strategies for addressing microarray cross-hybridization likewise apply here. For example, results for probes 26 and 45 in FIG. 3 suggest that more stringent thermo-affinity washes may reduce S:N ratios below a 1.2 (or other user-defined) threshold. Results from flow-through renewable microcolumn sample preparation studies consistently indicate that nucleic acid capture efficiency and purity is not negatively influenced by short contact times[15,20]. Hybridization kinetics (i.e. short contact times in the thermo-affinity chip and nonequilibrium microarray hybridization protocols) likely influence the specificity and S:N ratios of a microarray. Thermo-affinity purification in a gel-based sub-circuit can remove soluble environmental sample components that interfere with common fluorescent reporters.

Example 1

Nucleic Acid Sample Purification and Enrichment with a Thermo-Affinity Microfluidic Sub-Circuit. A microfluidic, thermo-affinity sub-circuit and method for target nucleic acids purification from admixtures prior to microarray hybridization and analysis are presented. The proof-of-principle results and thermo-affinity approach providing a new, relatively simple method for incorporating nucleic acid sample preparation into microfluidic structures and analysis systems are described. Synthetic gene targets were effectively enriched from sample admixtures at a ratio of 1 target to 10,000 non-target molecules.

Average signal/noise ratios for non-target microarray probes significantly improved after multiplexed thermo-affinity sample purification. With the accelerated development and use of nucleic acid microarray technology, there is considerable interest in applying existing (off-the-shelf) microarray methods and devices in uncharacterized sample backgrounds, and developing microfluidic devices for near-instantaneous biodetection applications. Uncharacterized sample backgrounds create both a sample preparation and data interpolation challenge for diagnostic use of microarray technology, and a significant engineering challenge for packaging microarray processes within a sample-to-answer fluidic test cartridge. The challenges become even more acute within the context of environmental monitoring due to the co-extraction of soluble environmental constituents that interfere with molecular techniques (including PCR amplification, hybridization, and fluorescent detection) and the preponderance of unknown and uncharacterized non-target organisms in the biological background.

Theoretical and experimental data with planar and gel element arrays show that mismatched targets preferentially bind under nonequilibrium hybridization conditions, exacerbating the problem of false positive detection. Depending upon the nucleic acid purification and labeling strategy, non-target sequences can also contribute to increased local and global background, degrading overall system (sample-to-answer) performance and dynamic range. One strategy to address cross-hybridization in defined (or closed) biological systems is to remove unpredictable probes from the array. Another is to increase the total number of probes on an array and statistically compare the signal intensity between perfectly matched (PM) and single base mismatched (MM) duplexes, typifying re-sequencing array designs. Hybridization kinetics can also be used to de-convolve false-positives in defined biological systems, and temperature, ionic strength and chemical additives are well-known methods of influencing hybridization stringency. However, the question concerning the application of microarray technology in uncharacterized samples or open biological systems is: how is it possible to know if and when hybridization signals result from a perfectly matched or mismatched probe:target combination? In an uncharacterized sample, any detectable microarray signal (over background) may have practical importance (e.g. pathogen surveillance), and recent work indicates how PM and MM probe comparisons can problematic (e.g. erroneous) in complex samples.

One approach to de-convolve false positive hybridizations on microarray substrates has been to generate post-hybridization thermal dissociation curves for every probe on the array 8-13. Historically, dissociation studies were aimed at understanding nucleotide mismatch discrimination, duplex stability and hybridization behavior in order to define an a priori hybridization condition for generating unambiguous reads from the initial hybridization data. Another way to utilize on-chip thermal dissociation, however, is as a post-hybridization, diagnostic indicator of hybridization specificity, utilizing curve shape and/or dissociation constants 8 as part of the decision logic for data interpretation, being careful to account for thermal effects on commonly used fluorescent reporters.

From a sensors or biodetection technology perspective, post-hybridization thermal dissociation analysis is an exciting possibility for target-independent, diagnostic validation of hybridization specificity irrespective of a priori knowledge of target background. By itself, however, the technique does little to address the (fluidic or automated) nucleic acid sample preparation challenge or simplify the attendant analysis instrumentation. Based on the inventor's prior work with oligonucleotide-coated particles as automated affinity purification matrices multiplexed affinity purification and thermal dissociation prior to biochip hybridization would simplify uncharacterized sample admixtures, thereby minimizing or eliminating sample interferents, improving hybridization specificity on a microarray detector, and minimizing or eliminating the need for post-hybridization thermal dissociation analysis. An integrated thermo-affinity sample preparation sub-circuit for sample purification and enrichment was developed that is consistent with a field portable form factor and analytical processes, and test evaluate the efficacy of thermo-affinity sample preparation on model admixtures of varying complexity.

Materials and Methods

Synthetic probes and targets. All capture probes and synthetic targets (Table 1) were synthesized with standard phosphoramidite chemistry. All oligonucleotides containing a 3'-terminal amino group were synthesized on a 3'-Amino-Modifier C7 CPG 500 (Glen Research Corporation, Sterling, Va., US). Deprotected oligonucleotides were purified by reverse phase HPLC (Dinamax; Rainin Instrument Co., Inc.), evaporated to dryness and reconstituted in ultrapure Milli-Q water to final concentration of 2 mM. Probes were stored at −20° C. until use. Complementary oligonucleotides, synthetic gene targets, and an aliquot of the random 20-mer background mixture ($dN_{20}$) were labeled with Texas Red sulfonyl chloride according to the manufacturer's protocol (Invitrogen Corporation, Carlsbad, Calif.) and purified by reverse phase HPLC before use.

Figure 1:
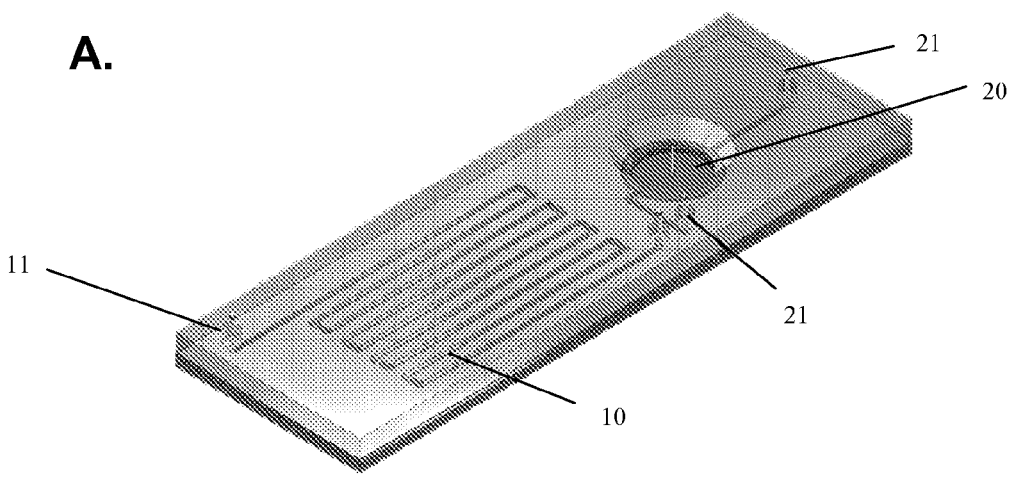
FIG. 1 illustrates a thermo-affinity sample preparation and microarray hybridization sub-circuit (A) and an experimental set-up (B).
Figure 1:
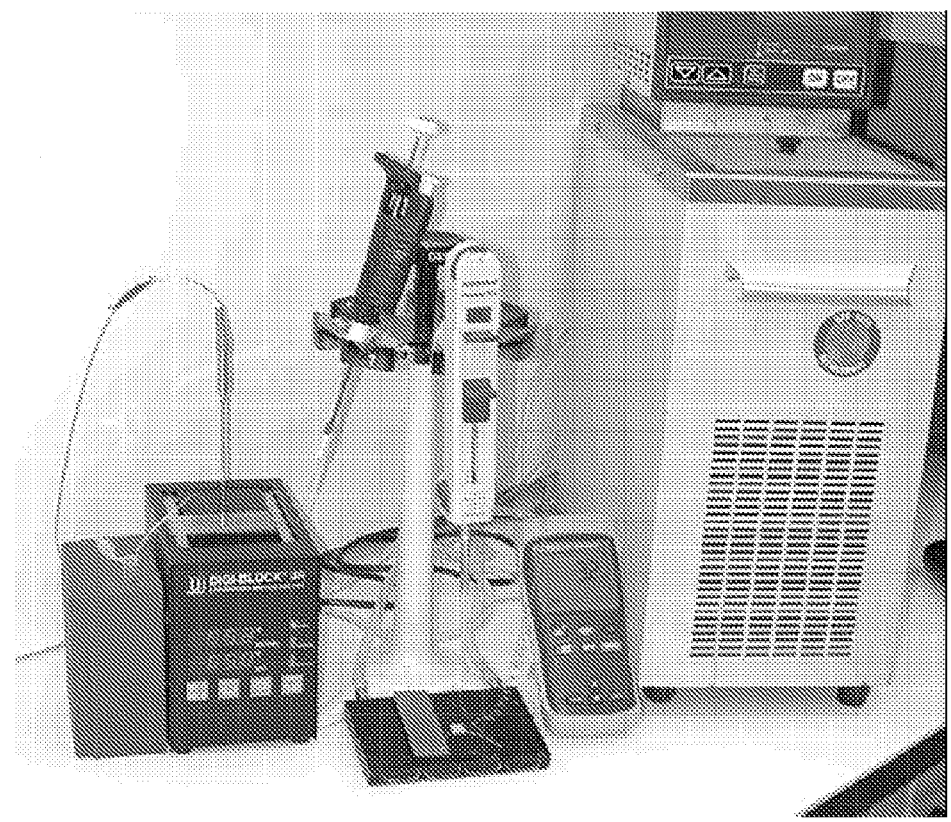

Thermo-affinity sample preparation sub-circuit. The sample preparation and microarray sub-circuit is illustrated in FIG. 1, and contains a serpentine channel 10 for thermo-affinity sample cleanup and target enrichment, and a separate gel element microarray chamber 20. The first inlet port 11 is used for sample and buffer delivery into the thermo-affinity reaction zone, and second inlet ports 21 is used to deliver enriched and purified sample to the hybridization chamber. The gel element array and a polymeric, serpentine thermo-affinity purification circuit were fabricated via photopolymerization. The microarray contained a 13×13×4 grid of gel element features of 100×100×20 microns each (676 total gel elements per array); the continuous serpentine gel was 300× 20 microns in cross-section and 28.8 cm in total length; the serpentine channel was approximately 550×540 microns in cross section and 28.8 cm in total length, with a free solution volume of approximately 70 μl. Microarray capture probes (at 2 mM concentration) in ultra-pure water were loaded at 1 mL per gel element using a custom-designed, non-contact printing robot. Fluorescent beacons served as internal controls for cross-linking efficiency and positional reference markers. Each probe was immobilized in four replicate gel elements per array, and integrated optics on the printing robot ensured that each and every gel element was successfully loaded with capture probe.

The multiplexed thermo-affinity sample preparation sub-circuit was loaded by pre-mixing all capture probes (except probe 52, which served as a negative control) at equimolar concentration (0.2 mM each) and filling the serpentine channel with the capture probe mixture. After a 15 min incubation at room temperature, the probe mixture was removed from the channel. Loaded sub-circuits (inclusive of the microarray) were then treated with a 0.1 M pyridine-borane complex in chloroform to chemically crosslink capture probes to the polymer matrices. Crosslinked matrices were subsequently treated with 0.1 M sodium borohydride aqueous solution, and subsequently washed in 0.1×SSPE, 0.1% SDS pH 7.2 and water to remove any unbound capture probes. The functional sub-circuits were then airdried in a dust-free environment and stored indefinitely in the dark at room temperature until use.

Thermo-affinity sample purification. The temperature over the sample preparation sub-circuit was controlled with a thermal plate, external refrigerated water bath and heat block, respectively. Solution temperature over the biochip was monitored with an embedded thermocouple. Fluid flow over the sample preparation and microarray portions of the sub-circuit were controlled by an Eppendorf digital pipette. Sample purification and enrichment was accomplished by first injecting target mixtures (~15 μL) into a pre-wetted thermoaffinity sub-circuit and incubating at 4° C. for up to 10 hours in a binding solution of 1M guanidine isothiocyanate, 50 mM HEPES pH 7.5, 5 mM $Na_2$ EDTA pH 8.0, 0.02% BSA, moving the target bolus to a fresh zone in the thermo-affinity serpentine channel at 15 min and 30 min before parking the solution over the last capture zone. Unbound nucleic acids were removed with a continuous 5 min wash in binding solution (100 μL), and nonspecifically bound nucleic acids thermally desorbed from the affinity enrichment channel at 37° C. for 1 hour in binding solution (100 μL). Desorbed nucleic acids were eluted with two successive washes in binding solution at 37° C. for 5 min and room temperature for 10 min (100 μL each wash). Thereafter, tightly bound nucleic acids were thermally desorbed from the thermo-affinity purification channel at 85° C. for 10 min in 45 μL binding solution.

Thermo-affinity purified and enriched nucleic acid targets were aspirated from the enrichment channel, 10 μL manually injected into the microarray portion of the sub-circuit (representing 5-10% of the total, purified fraction), and hybridized overnight at room-temperature in binding solution. After hybridization, arrays were washed in a High-Throughput Wash Station (Telechem, Sunnyvale, Calif.) with 6×SSPE containing 0.01% Triton X-100 for 5 minutes with stirring. The biochips were then briefly rinsed with Milli-Q water to remove residual salt, air dried and imaged on a custom, portable biochip imager 17 equipped with two 532 nm diode lasers and a 605 nm emission filter. Raw signal intensities were corrected for local background by subtracting the integrated signal intensity from the glass substrate surrounding each gel element. Thereafter, signal to noise ratios (S:N) were calculated as ((S1−N)/N)), where S=the average absolute signal for probe i over a minimum of 12 pseudoreplicates, and N is the average absolute signal for empty gel elements (n=85 empty gel elements surrounding the microarray capture probes). Results are presented as the average S:N ratio for 3 or 4 independent sub-circuits and array hybridizations, where ratios >1 are indicative of a detectable hybridization event. From prior work with gel element arrays and automated decision logic 18, 19, S:N ratios >1.2 are conservative, reproducible and robust indicators of positive hybridization and unambiguous mismatch discrimination for matched probe pairs, so this threshold was utilized for interpreting the data shown here. Other thresholds may be applied to the data (e.g. 3 SD over average background signal) and/or derived empirically for new arrays and probe sets, depending on the end use of the array and attendant biological question. The relative success and efficacy of the sample preparation sub-circuit was evaluated by analyzing false positive and false negative hybridizations, S:N ratios, and correlating microarray profiles with the CORREL function in Microsoft Excel.

PUBLICATIONS CITED

These publications are incorporated by reference to the extent they relate materials or methods disclosed herein.

A. D. Nucl. Acids Res. 1998, 26, 1515-1521.
Bavykin, S. G.; Akowski, J. P.; Zakhariev, V. M.; Barksy, V. E.; Perov, A. N.; Mirzabekov, A. D. Appl. Environ. Microbiol. 2001, 67, 922-928.
Bavykin, S. G.; Lysov, Y. P.; Zakhariev, V.; Kelly, J. J.; Jackman, J.; Stahl, D. A.; Cherni, A. J. Clin. Microbiol. 2004, 42, 3711-3730.
Bhanot, G.; Louzoun, Y.; Zhu, J.; DeLisi, C. Biophys. J. 2003, 84, 124-135
Bruckner-Lea, C. J.; Stottlemyre, M. S.; Holman, D. A.; Grate, J. W.; Brockman, F. J.; Chandler, D. P. Anal. Chem. 2000, 72, 4135-4141.
Chandler, D. P.; Jarrell, A. E. Appl. Environ. Microbiol. 2004, 70, 2621-2631.
Chandler, D. P.; Jarrell, A. E. BioTechniques 2005, 38, 591-600.
Chandler, D. P.; Schuck, B. L.; Brockman, F. J.; Bruckner-Lea, C. J. Talanta 1999, 49, 969-983.
Dai, H.; Meyer, M.; Stepaniants, S.; Ziman, M.; Stoughton, R. Nucl. Acids Res. 2002, 30, e86.
Fotin, A. V.; Drobyshev, A. L.; Proudnikov, D. Y.; Perov, A. N.; Mirzabekov,
Li, E. S. Y.; Ng, J. K. K.; Wu, J.-H.; Liu, W.-T. Environ. Microbiol. 2004, 6, 1197-1202.
Liu, W. T.; Mirzabekov, A. D.; Stahl, D. A. Environ. Microbiol. 2001, 3, 619629
Liu, W.-T.; Wu, J.-H.; Li, E. S.-Y.; Selamat, E. S. Appl. Environ. Microbiol. 2005, 71, 6453-6457.
Livshits, M. A.; Florentiev, V. L.; Mirzabekov, A. D. J Biomol. Struct. Dynam. 1994, 11, 783-795.
Livshits, M. A.; Mirzabekov, A. D. Biophys. J. 1996, 71, 2795-2801.
Smidt, H.; Yershov, G. M.; Stahl, D. A. Appl. Environ. Microbiol. 2003, 69, 2377-2382.
Stults, J. R.; Snoeyenbos-West, O.; Methe, B.; Lovley, D. R.; Chandler, D. P. Appl. Environ. Microbiol. 2001, 67, 2781-2789.
Tebbe, C. C.; Vahjen, W. Appl. Environ. Microbiol. 1993, 59, 2657-2665.
Wick, L. M.; Rouillard, J. M.; Whittam, T. S.; Gulari, E.; Tiedje, J. M.; Hashsham, S. A. Nucl. Acids Res. 2006, 34, e26. El Fantroussi, S.; Urakawa, H.; Bernhard, A. E.; Kelly, J. J.; Noble, P. A.;
Yershov, G.; Alferov, O.; Kukhtin, A.; The University of Chicago: U.S. Pat. No. 6,620,623, 2003.
Yershov, G.; Barsky, V.; Belgovskiy, A.; Kirillov, E.; Kreindlin, E.; Ivanov, I.; Parinov, S.; Guschin, D.; Drobishev, A.; Dubiley, S.; Mirzabekov, A. Proc. Natl. Acad. Sci. USA 1996, 93, 4913-4918.

TABLE 1

Synthetic Probes and Targets[a]

| Capture probe ID (5'-3') | | Relationship to Synthetic Targets[b] |
|---|---|---|
| 1. CTTTRGAAAATAIGAGATAATT | (SEQ ID NO: 1) | NC |
| 2. TTGAGTAAATAGGRTATAATTG | (SEQ ID NO: 2) | PM |

TABLE 1-continued

Synthetic Probes and Targets[a]

| | | | |
|---|---|---|---|
| 3. | TTGAGTARATAAGATATAACTG | (SEQ ID NO: 3) | PC |
| 4. | TTACCCGATTCCRGGTTAATT | (SEQ ID NO: 4) | PC |
| 5. | TTACCCGATTCTRGGTTAATT | (SEQ ID NO: 5) | PM-T |
| 6. | GAGGRTAYACGAATTACTAC | (SEQ ID NO: 6) | NC |
| 7. | GTATTTCCGCATTGTGAYGC | (SEQ ID NO: 7) | NC |
| 8. | GTATTTTCGCATTGAGAYGC | (SEQ ID NO: 8) | NC |
| 9. | TATACGTTCGTGTGCAGT | (SEQ ID NO: 9) | PC |
| 10. | GTAAATCTGTTCTATGCTGT | (SEQ ID NO: 10) | PC |
| 11. | CTTAARAAAACGAGTGATAATT | (SEQ ID NO: 11) | PC |
| 12. | YCTGTTACAGTGTTTAATAGTTT | (SEQ ID NO: 12) | PC |
| 13. | AAACTTGYCAAAGCTGTYAGA | (SEQ ID NO: 13) | PM-T |
| 14. | TTGATAATTRCATTACGGCTA | (SEQ ID NO: 14) | PC |
| 15. | TTGATAATCACATTRCGGCTA | (SEQ ID NO: 15) | PC |
| 16. | TAATIAYGAGACTTCTCCAGT | (SEQ ID NO: 16) | PC |
| 17. | TTTTACGATTGCCTTTYTGGATA | (SEQ ID NO: 17) | NC |
| 20. | GTTATAATGATTGTAGTATCC | (SEQ ID NO: 18) | NC |
| 21. | TTGAATTGAATARTTCGTAGT | (SEQ ID NO: 19) | PC |
| 22. | AAATGCTAAGCATGAATATGG | (SEQ ID NO: 20) | PM-T |
| 23. | AGATGCTAAGCAYGAGTATGG | (SEQ ID NO: 21) | PC |
| 24. | AGTCIGATAATAYTTGGAYGTA | (SEQ ID NO: 22) | NC |
| 25. | TTTCTAATACATSGGTIAATTTGAG | (SEQ ID NO: 23) | PC |
| 26. | ATAGGCAATGGGRCTGATA | (SEQ ID NO: 24) | PM |
| 27. | GITTATTTGCAGTTAARGGG | (SEQ ID NO: 25) | PC |
| 28. | GTTTATTCGCAGTTAARGGG | (SEQ ID NO: 26) | PM |
| 29. | CACTGTTGTAGCAAATAGG | (SEQ ID NO: 27) | PM-T |
| 30. | TCGTTTAGAGGTGACGTCYT | (SEQ ID NO: 28) | PM |
| 31. | RCATAAATATAAACATAGTGTG | (SEQ ID NO: 29) | PC |
| 32. | ACCTAAAATCACGCAAAGGATATCAA | (SEQ ID NO: 30) | PC |
| 33. | ATYGATATTRCATCRTTAACAAG | (SEQ ID NO: 31) | PM |
| 34. | AAAAYCATCTGAYTAATTATTCTATA | (SEQ ID NO: 32) | PC |
| 35. | TCACAATAATTTAAAATGCTCT | (SEQ ID NO: 33) | NC |
| 36. | GTCGTCAATAGCATTAATAATAC | (SEQ ID NO: 34) | PC |
| 37. | GTAGCCAATAGCGTTAATAATA | (SEQ ID NO: 35) | PC |
| 38. | GATGCTAATGATATATTTCCATA | (SEQ ID NO: 36) | PM-T |
| 39. | ACRTTCTATTGTGAAGGTGCYTC | (SEQ ID NO: 37) | PC |
| 40. | ATATTTCAAGCYCCATAGTAG | (SEQ ID NO: 38) | PC |
| 41. | GAGTGCCCTAATCCAGTG | (SEQ ID NO: 39) | PC |
| 42. | CTGTGTTCTTAGGTATTATG | (SEQ ID NO: 40) | PC |
| 43. | ATTGCTTACGGAGGTGATTTTG | (SEQ ID NO: 41) | PC |

TABLE 1-continued

Synthetic Probes and Targets[a]

| | | | |
|---|---|---|---|
| 44. | ATCATTTCCATGTAGAGTTGC | (SEQ ID NO: 42) | PC |
| 45. | TCTTYTGCACCCTARTCYATTTGA | (SEQ ID NO: 43) | PM-T |
| 46. | GTYCAATTCTACCTTCTATGA | (SEQ ID NO: 44) | NC |
| 47. | GACTTGRAGAGGTACRTTTTC | (SEQ ID NO: 45) | NC |
| 48. | GACTTGGAGAAGTACATTTTC | (SEQ ID NO: 46) | PM-T |
| 49. | GCATTRCTTCTCTGAATGAAT | (SEQ ID NO: 47) | PC |
| 50. | AGTTAGTTGTAATCCACTATAC | (SEQ ID NO: 48) | PM |
| 51. | ATTTTGCGATCAATATACACAT | (SEQ ID NO: 49) | PM-T |
| 52. | GATGATGATGATGATGATGA | (SEQ ID NO: 50) | PM |
| 1707. | TCAAGAGTTGCCCATCCTGCAGCAA | (SEQ ID NO: 51) | eaeA3 |
| 1708. | AACATCGCTCTTGCCACAGACTGCGTCAGT | (SEQ ID NO: 52) | stx1 |
| 1709. | CCAGTGAGTGACGACTGATTTGCATTCCGG | (SEQ ID NO: 53) | stx2 |
| 1710. | TGCGATCAGGAAATCAACCAGA | (SEQ ID NO: 54) | invA antisense |
| 1711. | TCTGGTTGATTTCCTGATCGCA | (SEQ ID NO: 55) | invA sense |

| Synthetic oligonucleotide targets (5' to 3')[d] | | | Complementary Probe on chip |
|---|---|---|---|
| 421 | CAATTATAYCCTATTTACTCAA | (SEQ ID NO: 56) | 2 |
| 448. | TATCAGYCCCATTGCCTAT | (SEQ ID NO: 57) | 26 |
| 425. | CCCYTTAACTGCGAATAAAC | (SEQ ID NO: 58) | 28 |
| 429. | ARGACGTCACCTCTAAACGA | (SEQ ID NO: 59) | 30 |
| 430. | CTTGTTAAYGATGYAATATCRAT | (SEQ ID NO: 60) | 33 |
| 432. | GTATAGTGGATTACAACTAACT | (SEQ ID NO: 61) | 50 |
| 476. | TTTTTAATTAACCYAGAATCGGGTAATTTTT | (SEQ ID NO: 62) | 5 |
| 477. | TTTTTTTTTTTCAAATRGAYTAGGGTGCARAAGATTTTTTTTTT | (SEQ ID NO: 63) | 45 |
| 478. | TTTTTTTTTTTTTTTCTRACAGCTTTGRCAAGTTTTTTTTTTTTTTTT | (SEQ ID NO: 64) | 13 |
| 479. | TTTTTTTTTTTTTTTTTTCCTATTTGCTACAACAGTGTTTTTTTTTTTTTTTTTT | (SEQ ID NO: 65) | 29 |
| 480. | TTTTTTTTTTTTTTTTTTATGTGTATATTGATCGCAAAATTTTTTTTTTTTTTT | (SEQ ID NO: 66) | 51 |
| 481. | TTTTTTTTTTTTTTCCATATTCATGCTTAGCATTTTTTTTTTTTTTTTT | (SEQ ID NO: 67) | 22 |
| 482. | TTTTTTTTTTTATGGAAATATATCATTAGCATCTTTTTTTTTTT | (SEQ ID NO: 68) | 38 |
| 483. | TTTTTGAAAATGTACTTCTCCAAGTCTTTTT | (SEQ ID NO: 69) | 48 |
| 484. | TCATCATCATCATCATCATC (hybridization marker) | (SEQ ID NO: 70) | 52 |

Model PCR primers:

| | | | |
|---|---|---|---|
| eaeA3: | 5'-TR-CAATTTTTCAGGGAATAACATTG<br>5'-AAAGTTCAGATCTTGATGACATTG | (SEQ ID NO: 71) and<br>(SEQ ID NO: 72) | |
| stx1: | 5'-TR-TCTTATCTGGATTTAATGTCGC<br>5'-TCAGCTGTCACAGTAACAAACC | (SEQ ID NO: 73) and<br>(SEQ ID NO: 74) | |
| stx2: | 5'-TR-TTATACCACTCTGCAACGTGTC<br>5'-AACTCCATTAACGCCAGATA | (SEQ ID NO: 75) and<br>(SEQ ID NO: 76) | |

| Synthetic gene targets (5' to 3')[c,d] | | | Complementary Probe |
|---|---|---|---|
| eaeA3: | CAATTTTTCAGGGAATAACA<u>TTGCTGCAGGATGGGCAACTCTTGA</u>GCT<br>TCTGTAAATATAAATTTAATTAAGAGAAAATACAATGTCATCAAGATCTGAACTTT-TR | (SEQ ID NO: 77)<br>(SEQ ID NO: 78) | 1707 |

TABLE 1-continued

Synthetic Probes and Targets[a]

| | | | |
|---|---|---|---|
| stx1: | TCTTATCTGGATTTAATGTCGCATAGTGGAACCTC<u>ACTGACGCAGT</u> | (SEQ ID NO: 79) | 1708 |
| | CTGTGGCAAGAGCGATGTTACGGTTTGTTACTGTGACAGCTGA-TR | (SEQ ID NO: 80) | |
| stx2: | TTATACCACTCTGCAACGTGTCGCAGCGCTGGAACGTT<u>CCGGAATGC</u> | (SEQ ID NO: 81) | 1709 |
| | AAATCAGTCGTCACTCACTGGTTTCATCATATCTGGCGTTAATGGAGTT-TR | (SEQ ID NO: 82) | |

[a]Probe and target sequences were all synthesized with a 3'-NH₂ and HPLC purified. Sequences conform to IUPAC nomenclature where I = inosine; R = A or G; Y = C or T; S = C or G; N = A, C G or T.
[b]PM = perfect match with a synthetic target; PM-T = perfect match with a synthetic target containing T-tails; PC = partially complementary to at least one synthetic target; NC = not complementary to any target.
[c]TR = Texas Red; LR = Lissamine Rhodamine. Beacons are for positional reference and a control for oligonucleotide crosslinking during microarray manufacture.
[d]Synthetic targets were synthesized with a 3'-NH₂ and subsequently labeled with Texas Red sulfonyl chloride. Underlines in synthetic genes indicate the region of complementarity to the capture probe.

TABLE 2

Ratio-metric comparison of signal:nonsense intensity ratios for perfectly matched probe:target combinations. Results are the average from 3 independent trials. Grey boxes highlight a decreased signal:nonsense ratio relative to the initial target mixture. PM = perfect match probe:target combinations; PM-T = perfect match probe-target combinations where the target contains a T-tail (refer to Table 1).

| | Probe ID | | | | | | | | | | | | | |
|---|---|---|---|---|---|---|---|---|---|---|---|---|---|---|
| | PM | | | | | | | PM-T | | | | | | |
| | 30 | 2 | 50 | 33 | 26 | 28 | 52 | 48 | 22 | 13 | 51 | 5 | 45 | 29 | 38 |
| Mix of all possible 20 mers | 1.6 | 0.4 | 0.6 | 0.7 | 3.1 | 0.4 | 1.2 | 0.7 | 0.4 | 1.1 | 0.7 | 0.5 | 3.1 | 1.2 | 0.4 |
| Pure target mixture | 19.0 | 12.1 | 15.5 | 17.4 | 16.0 | 11.9 | 21.6 | 13.5 | 7.6 | 8.3 | 6.9 | 9.2 | 12.9 | 13.8 | 12.0 |
| Initial mix (targets + background) | 3.1 | 2.0 | 2.7 | 2.3 | 3.5 | 1.7 | 3.8 | 2.1 | 1.0 | 1.4 | 1.7 | 1.4 | 4.2 | 1.8 | 1.4 |
| Enriched sample | 6.9 | 1.4 | 2.0 | 2.0 | 10.0 | 1.4 | 1.2 | 2.3 | 1.2 | 3.7 | 1.7 | 2.8 | 6.9 | 2.5 | 1.4 |
| Enriched, no thermal wash | 1.8 | 1.6 | 1.2 | 1.2 | 1.4 | 1.3 | 1.1 | 1.2 | 1.2 | 1.1 | 1.1 | 1.3 | 1.4 | 1.2 | 1.0 |

We claim:

1. A sample preparation and microarray microfluidic sub-circuit for purifying perfect match (PM) target nucleic acids from a sample, prior to biochip hybridization, the subcircuit comprising:
   (a) a serpentine channel including a thermo-affinity reaction zone comprising a plurality of capture probes within the serpentine channel, wherein the thermo-affinity reaction zone is configured to receive a sample comprising PM target and mismatch (MM) nucleic acids through a first inlet port, and to hold the sample at a first predetermined temperature, wherein the temperature of the sample is progressively increased as the sample moves through the thermo-affinity reaction zone, and wherein the nucleic acid targets in the sample are purified by binding of MM nucleic acids to the capture probes as the sample flows through the thermo-affinity reaction zone; and
   (b) a gel element microarray chamber fluidly coupled to the thermo-affinity reaction zone configured to receive the sample through a second inlet port after the purified sample has passed through the thermo-affinity reaction zone;
   (c) a temperature controller
   wherein said microarray exhibits an increase of signal-to-noise of PM over MM nucleic acids.

2. A method of multiplexed thermo-affinity purification of target nucleic acids prior to microarray hybridization and analysis, the method comprising:
   (a) obtaining an admixture comprising the target nucleic acids; and
   (b) using a sample preparation subcircuit as in claim 1 to purify the target nucleic acids.

3. A method to prepare a microarray for analysis of target nucleic acids, the method comprising:
   (a) obtaining an admixture comprising the target nucleic acids;
   (b) using a sample preparation sub-circuit as in claim 1 to purify the target nucleic acids; and
   (c) preparing the microarray by applying the purified target nucleic acids thereto the microarray.

4. The preparation and microarray microfluidic sub-circuit of claim 1 wherein the temperature controller comprises a thermal plate.

5. The preparation and microarray microfluidic sub-circuit of claim 1 wherein the temperature controller comprises a refrigerated water bath.

6. The preparation and microarray microfluidic sub-circuit of claim 1 wherein the temperature controller comprises a heat block.

7. The sample preparation and microarray microfluidic sub-circuit of claim 1 wherein nucleic acids in the sample are present in fmol quantities.

8. The sample preparation and microarray microfluidic sub-circuit of claim 1, wherein the sample preparation and microarray microfluidic sub-circuit is field-portable, and wherein the sample containing a target mixture for multiplexed template thermo-affinity preparation is injected into the thermo-affinity reaction zone, incubated in a binding solution, moved to a plurality of fresh zones in the thermo-affinity reaction zone at specified temporal intervals and parked, wherein unbound nucleic acids are washed out, and tightly bound nucleic acids are desorbed at elevated temperature, aspirated and injected into the microarray portion of the sub-circuit, where hybridization occurs using the thus purified sample.

9. The sample preparation and microarray microfluidic sub-circuit of claim 1 wherein the thermo-affinity reaction zone is configured to progressively increase the temperature of the sample in a plurality of step increases as the sample moves through the thermo-affinity reaction zone.

10. The sample preparation and microarray microfluidic sub-circuit of claim 9 wherein the thermo-affinity reaction zone is configured to progressively increase the temperature of the sample from about 4° C. to about 85° C. as the sample moves through the thermo-affinity reaction zone.

11. The sample preparation and microarray microfluidic sub-circuit of claim 10 wherein the incubation occurs at a first predetermined temperature of about 4° C.

12. The sample preparation and microarray microfluidic sub-circuit of claim 11 wherein the thermo-affinity reaction zone further comprises one or more capture zones.

13. The sample preparation and microarray microfluidic sub-circuit of claim 12 wherein the first capture zone is configured to hold the temperature of the sample at about 37° C.

14. The sample preparation and microarray microfluidic sub-circuit of claim 12 wherein the thermo-affinity reaction zone further comprises at least two capture zones.

15. The sample preparation and microarray microfluidic sub-circuit of claim 12 wherein a second purification zone is configured to hold the temperature of the sample at about 85° C.

* * * * *